(12) United States Patent
Sasaki

(10) Patent No.: US 10,931,603 B2
(45) Date of Patent: Feb. 23, 2021

(54) RELAY APPARATUS FOR TRANSMITTING DATA WRITTEN IN MEMORY UPON RECEIVING DATA ACQUISITION REQUEST COMMAND FROM CLIENT BEFORE PREDETERMINED TIME ELAPSES AFTER RECEPTION OF DATA FROM SERVER, AND FOR DETERMINING PROPERTY OF TRANSMITTING DATA ACQUISITION REQUEST COMMAND

(71) Applicant: OLYMPUS CORPORATION, Tokyo (JP)

(72) Inventor: Akinori Sasaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/438,609

(22) Filed: Jun. 12, 2019

(65) Prior Publication Data
US 2019/0297029 A1 Sep. 26, 2019

Related U.S. Application Data

(63) Continuation of application No. PCT/JP2017/036311, filed on Oct. 5, 2017.

(30) Foreign Application Priority Data

Dec. 13, 2016 (JP) .................................. 2016-241398

(51) Int. Cl.
*H04L 12/931* (2013.01)
*G16H 40/20* (2018.01)
(Continued)

(52) U.S. Cl.
CPC ........... *H04L 49/351* (2013.01); *G06Q 50/22* (2013.01); *G16H 40/20* (2018.01); *G16H 40/63* (2018.01); *H04L 49/40* (2013.01)

(58) Field of Classification Search
CPC ....... H04L 49/351; H04L 49/40; G06Q 50/22; G16H 40/20; G16H 40/63
See application file for complete search history.

(56) References Cited

U.S. PATENT DOCUMENTS 6,304,578 B1 * 10/2001 Fluss .................. H04L 12/2801
348/E7.063
9,769,333 B2 * 9/2017 Miyazawa ......... H04N 1/00244
(Continued)

FOREIGN PATENT DOCUMENTS

JP     2000-057041 A    2/2000
JP     2001-101061 A    4/2001
(Continued)

OTHER PUBLICATIONS

Japanese Office Action dated Apr. 2, 2019 in Japanese Patent Application No. 2018-556207.
(Continued)

*Primary Examiner* — Hoang-Chuong Q Vu
(74) *Attorney, Agent, or Firm* — Scully, Scott, Murphy & Presser, P.C.

(57) ABSTRACT

An event reception unit receives event identification information transmitted from a client. A recorder records event identification information and a data acquisition request command in association with each other. A command acquisition unit acquires a data acquisition request command associated with the event identification information received by the event reception unit. A command transmission control unit controls command transmission performed by a command transmission unit. A cache control unit writes, in a memory, data received from a management server. When a command reception unit receives a data acquisition request command transmitted from a client, a data transmission unit transmits the data written in the memory to the client.

10 Claims, 4 Drawing Sheets

(51) Int. Cl.
*G16H 40/63* (2018.01)
*G06Q 50/22* (2018.01)

(56) References Cited

U.S. PATENT DOCUMENTS

| | | | | |
|---|---|---|---|---|
| 2003/0088679 | A1* | 5/2003 | Hori | H04L 67/28 709/229 |
| 2004/0066789 | A1* | 4/2004 | Kobayashi | H04L 47/2433 370/402 |
| 2006/0098722 | A1* | 5/2006 | Tanaka | H04L 25/05 375/211 |
| 2007/0240006 | A1* | 10/2007 | Fung | G06F 1/32 713/323 |
| 2008/0040642 | A1* | 2/2008 | Furukawa | H04N 1/00244 714/746 |
| 2008/0178212 | A1* | 7/2008 | Kinoshita | H04L 12/2812 725/32 |
| 2011/0214133 | A1* | 9/2011 | Lum | G03G 15/502 719/318 |
| 2011/0276660 | A1* | 11/2011 | Nonaka | H04L 63/108 709/219 |
| 2013/0318236 | A1* | 11/2013 | Coates | H04L 41/22 709/224 |
| 2014/0129607 | A1* | 5/2014 | Nagumo | H04L 41/5048 709/201 |
| 2016/0065683 | A1* | 3/2016 | Saito | G06F 3/1267 709/203 |

FOREIGN PATENT DOCUMENTS

| | | |
|---|---|---|
| JP | 2002-373108 A | 12/2002 |
| JP | 2008-537814 A | 9/2008 |
| JP | 2009-064169 A | 3/2009 |
| JP | 2010-282430 A | 12/2010 |

OTHER PUBLICATIONS

International Search Report dated Jan. 9, 2018 issued in International Application No. PCT/JP2017/036311.

International Preliminary Report on Patentability dated Jun. 18, 2019, together with the Written Opinion received in related International Application No. PCT/JP2017/036311.

* cited by examiner

FIG.3

| EVENT ID | DATA ACQUISITION REQUEST COMMAND |
|---|---|
| POWERED ON | ORDER ACQUISITION REQUEST COMMAND |
| SCOPE CONNECTED | — |
| EXAMINATION STARTED | — |
| EXAMINATION ENDED | ORDER ACQUISITION REQUEST COMMAND |
| ORDER LIST DISPLAYED | — |
| POWERED OFF | — |

38

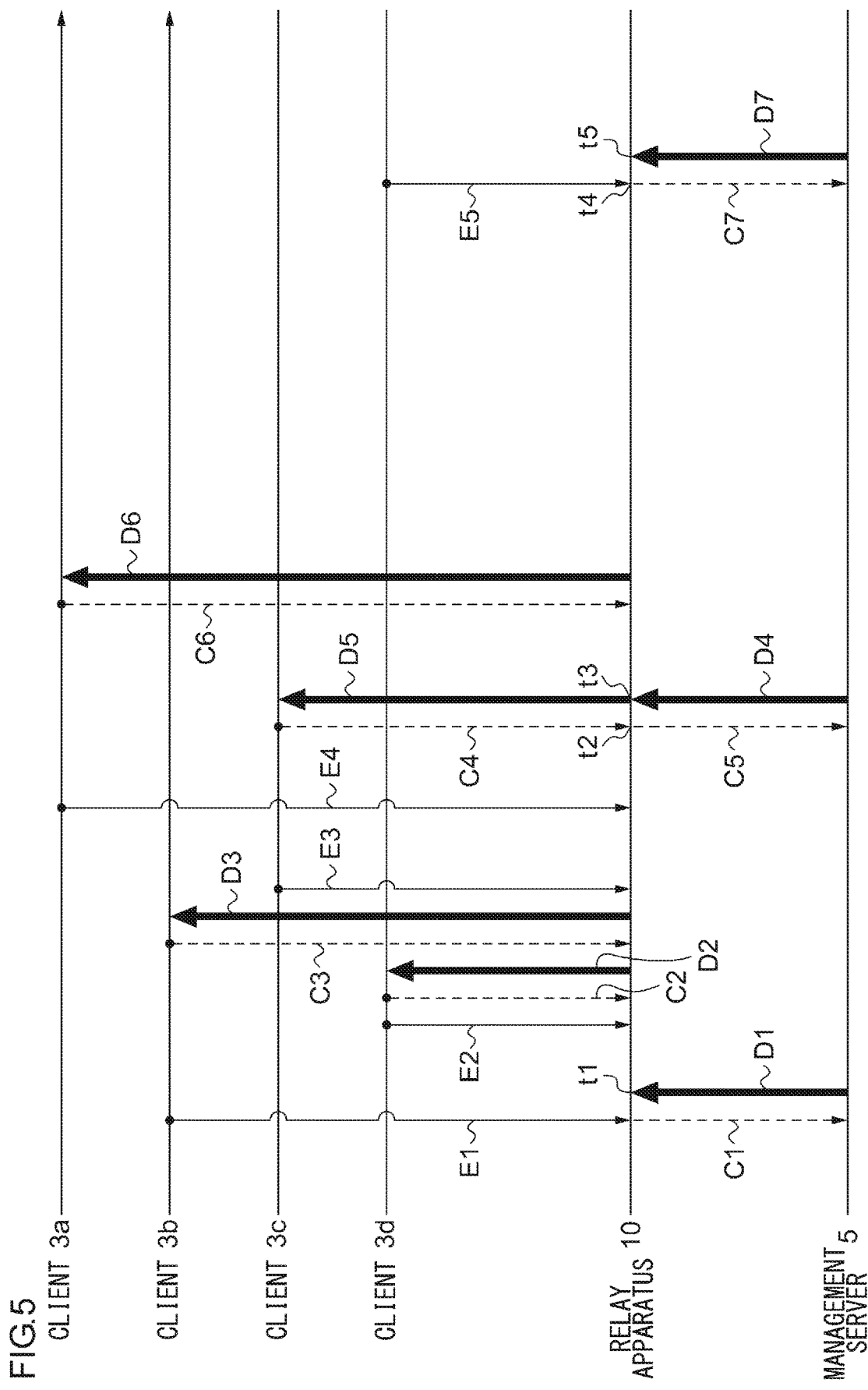

RELAY APPARATUS FOR TRANSMITTING DATA WRITTEN IN MEMORY UPON RECEIVING DATA ACQUISITION REQUEST COMMAND FROM CLIENT BEFORE PREDETERMINED TIME ELAPSES AFTER RECEPTION OF DATA FROM SERVER, AND FOR DETERMINING PROPERTY OF TRANSMITTING DATA ACQUISITION REQUEST COMMAND

CROSS-REFERENCE TO RELATED APPLICATIONS

This application is based upon and claims the benefit of priority from the prior Japanese Patent Applications No. 2016-241398, filed on Dec. 13, 2016, and International Application No. PCT/JP2017/036311, filed on Oct. 5, 2017, the entire contents of which are incorporated herein by reference.

BACKGROUND OF THE INVENTION

1. Field of the Invention

The present invention relates to a relay apparatus for relaying communication between a client and a server.

2. Description of the Related Art

Japanese Patent Application Publication No. 2009-64169 discloses a hospital information system in which a hospital information management server and a medical service support system are connected via a LAN (local area network). Cloud servers have been generalized in various fields due to the recent spread of cloud computing. Changing the arrangement form of hospital information management servers to a form where the servers are arranged outside the LAN has also been under consideration in medical facilities.

However, if a management server that has been connected to the LAN thus far in a medical facility is arranged outside the LAN, the possibility that the communication speed between the client and the management server becomes slow and that the communication becomes unstable is increased. Doctors have a very tight schedule, and if necessary data cannot be acquired from a management server located outside the LAN or if it takes time to acquire the data, there can be a situation where the work cannot be done as scheduled. Therefore, it is desirable to build a mechanism for efficiently acquiring data from a management server arranged outside the LAN.

SUMMARY OF THE INVENTION

In this background, a purpose of the present invention is to provide a technology for efficiently acquiring data from a management server arranged outside the LAN.

A relay apparatus according to one embodiment of the present invention relays communication between a client and a server and includes: a processor including hardware; and a recorder that records event identification information and a data acquisition request command in association with each other. The processor is configured to: receive event identification information transmitted from a client; acquire, from the recorder, a data acquisition request command associated with the event identification information that has been received; transmit the data acquisition request command to a server upon acquiring the data acquisition request command associated with the event identification information that has been received; receive data transmitted from the server in response to the data acquisition request command; write the data that has been received in a memory; receive a data acquisition request command transmitted from the client; and transmit the data written in the memory to the client.

Optional combinations of the aforementioned constituting elements and implementations of the invention in the form of methods, apparatuses, systems, recording mediums, and computer programs may also be practiced as additional modes of the present invention.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which:

FIG. 3 is a diagram illustrating an example of a mater table;

FIG. 5 is a diagram showing an example of a timing chart for event notification and command transmission.

DETAILED DESCRIPTION OF THE INVENTION

The invention will now be described by reference to the preferred embodiments. This does not intend to limit the scope of the present invention, but to exemplify the invention.

Figure 1:
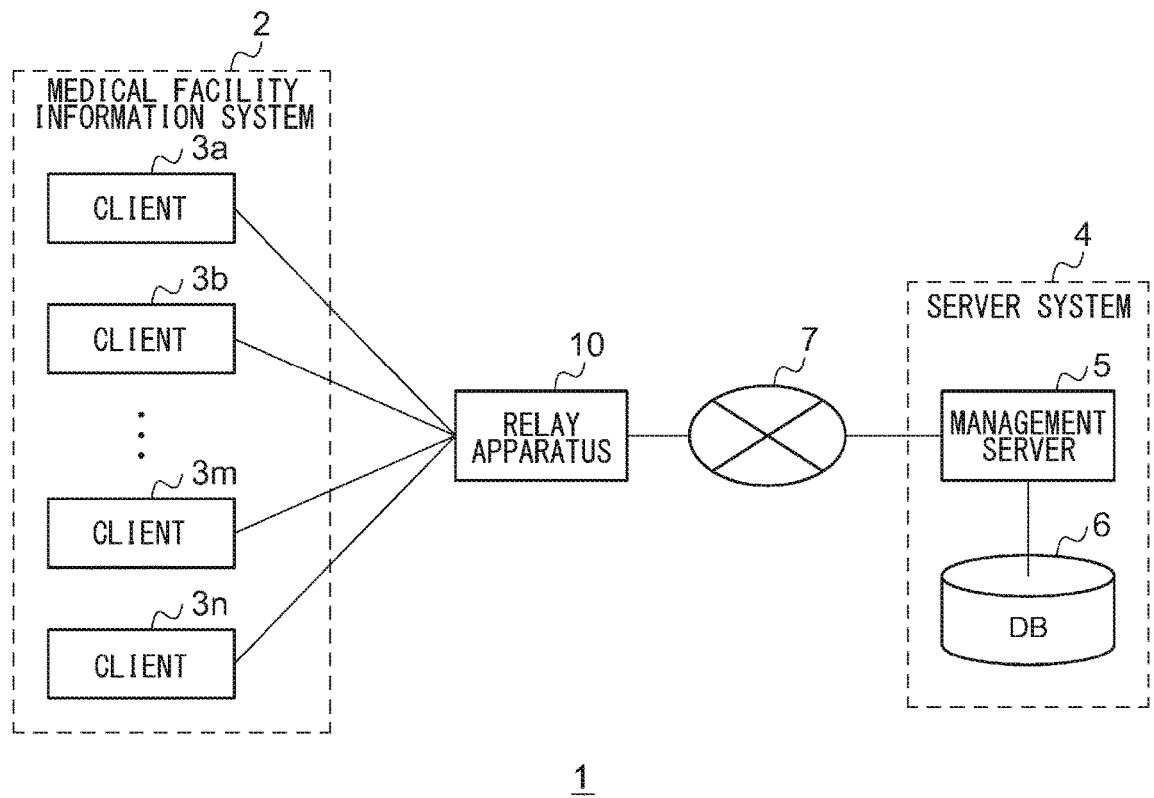
FIG. 1 is a diagram illustrating the configuration of an information processing system according to an embodiment.

FIG. 1 is a diagram illustrating the configuration of an information processing system 1 according to an embodiment of the present invention. The information processing system 1 includes a medical facility information system 2 having a plurality of clients 3a to 3n (hereinafter, referred to as "client 3" unless otherwise specified), a server system 4 having a management server 5 and a database (DB) 6, and a relay apparatus 10 for relaying communication between the clients 3 and the management server 5. The relay apparatus 10 is a router device, establishes a LAN (local area network) in the medical facility information system 2 so as to enable communication among the plurality of clients 3, and connects the LAN to an external network 7 so as to enable communication between the clients 3 and a device on a network 7.

The medical facility information system 2 according to the embodiment includes various types of clients 3 required to perform an endoscopic examination. A client 3 is a device connected to the LAN of the medical facility and includes an endoscopic observation apparatus for displaying and recording an endoscopic image captured by a scope, a cleaning machine for cleaning a used scope, a terminal device (personal computer) used for generating a report of an examination that has been completed, and the like. The client 3 communicates with the management server 5 outside the LAN via the relay apparatus 10.

The server system 4 is connected to the medical facility information system 2 via the network 7 such as the Internet. The management server 5 receives, from the medical facility information system 2, examination order data, an endoscopic image captured by the endoscopic observation apparatus, and the like, and records the order data, the endoscopic image, and the like in the DB 6. The management server 5 transmits the order data and the endoscope image recorded in the DB 6 to the relay apparatus 10 in response to a data acquisition request command transmitted from the relay apparatus 10.

The endoscope observation apparatus, which is a client 3, acquires the order data for the day from the management server 5 before the start of the examination and displays an order list on a display apparatus, and a medical worker selects order data for an examination to be performed now from the order list. By selecting the order data for the examination, an endoscopic image captured in an endoscopic examination to be performed now is linked to the order data and managed. A process of acquiring order data by the endoscopic observation apparatus is always performed before the start of each examination. However, if it takes time to acquire order data due to a communication failure between the relay apparatus 10 and the management server 5 or the like, a problem that the examination cannot be started arises. Further, the doctor reads all endoscopic images captured in the endoscopic examination from the management server 5 to the terminal apparatus in order to create an examination report after the examination is completed. If it takes time for the reading, the report creation task cannot be started readily.

In order to solve such a problem, the relay apparatus 10 according to the embodiment has a "function of acquiring data in advance" by receiving, in advance, data that will be required by the client 3 from the management server 5 in response to the occurrence of a predetermined event in the client 3 and caches the data in a memory. When the relay apparatus 10 receives a data acquisition request command from the client 3 after acquiring the data in advance, the relay apparatus 10 transmits the data cached in the memory to the client 3. Since the data requested through the data acquisition request command is already stored temporarily in the memory at the time when the relay apparatus 10 has received the data acquisition request command transmitted from the client 3, the relay apparatus 10 is able to transmit the data to the client 3 immediately.

Figure 2:
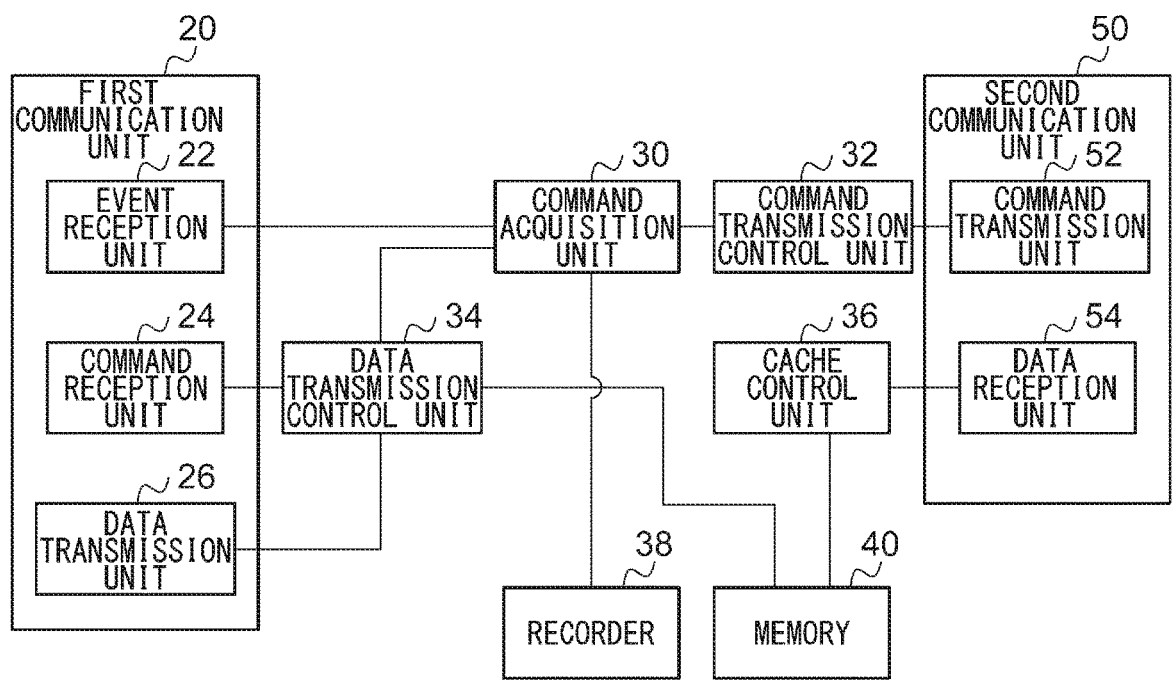
FIG. 2 is a diagram illustrating the configuration of a relay apparatus.

FIG. 2 illustrates the configuration of the relay apparatus 10. The relay apparatus 10 includes a first communication unit 20, a command acquisition unit 30, a command transmission control unit 32, a data transmission control unit 34, a cache control unit 36, a recorder 38, a memory 40, and a second communication unit 50.

In FIG. 2, the elements shown in functional blocks that indicate a variety of processes are implemented in hardware by any circuit block, a main memory, other LSI's, or the like, and in software by a program loaded in main memory, etc. Thus, a person skilled in the art should appreciate that there are many ways of accomplishing these functional blocks in various forms in accordance with the components of hardware only, software only, or the combination of both, and the way of accomplishing these functional blocks is not limited to any particular one.

Although various types of clients 3 are installed in a medical facility, a case where the clients 3 are endoscopic observation apparatuses will be used as an example in the following. FIG. 3 shows an example of the master table recorded in the recorder 38. The recorder 38 records a master table for each type of the clients 3. FIG. 3 shows a master table for an endoscope observation apparatus. The recorder 38 also records a master table for a cleaning machine and a master table for a terminal apparatus.

The master table associates and records event identification information for identifying an event that may occur in the endoscope observation apparatus and a data acquisition request command. The event is preset for a predetermined conditional change in the endoscopic observation apparatus, and the endoscopic observation apparatus has a function of automatically transmitting information for identifying the event indicating the conditional change (hereinafter, referred to as "event ID") when the predetermined conditional change occurs.

In the master table shown in FIG. 3, "powered on", "scope connected", "examination started", "examination ended", "order list displayed", and "powered off" are set as events of the endoscope observation apparatus. In the actual master table, a character string that is a combination of alphabets and numbers may be used as an event ID.

The endoscope observation apparatus has a functional module that automatically detects the occurrence of each event set in the master table. For example, "powered on" and "powered off" events are detected by a power management module. The "scope connected" event is detected by a scope management module, which acquires an electrical signal when the scope is connected. The "examination started" event, the "examination ended" event, and the "order list displayed" event are detected by an operation monitoring module, which monitors operation input to an input interface (such as a keyboard or a mouse) entered by a medical worker. When a client 3 that includes the endoscope observation apparatus according to the embodiment detects the occurrence of an event that has been set, the client 3 transmits its event ID to the relay apparatus 10.

In the master table shown in FIG. 3, an "order acquisition request command" is associated with the "powered on" event and the "examination ended" event, and no data acquisition request command is associated with other events. The "order acquisition request command" is a command for requesting the acquisition of all order data for the day. Upon being notified of the event ID from the client 3, when a data acquisition request command is associated with the event ID as notified, the relay apparatus 10 transmits the data acquisition request command to the management server 5. In this example, when notified of the event ID for "powered on" or the event ID for "examination ended", the relay apparatus 10 transmits an order acquisition request command to the management server 5.

The endoscope observation apparatus is in a power-off state before the start of the examination task for a day, and the power is turned on when the examination task is started. Further, when one endoscopic examination is ended, the endoscopic observation apparatus prepares to start the next endoscopic examination. Before the start of the endoscopic examination, the endoscopic observation apparatus acquires all order data for the day and displays an order list on the display apparatus. Therefore, after the power of the endoscopic observation apparatus is turned on and after the endoscopic examination is ended, the endoscopic observation apparatus is very likely to carry out a process of acquiring all the order data. Therefore, in the master table, the "powered on" event and the "examination ended" event are recorded in association with the "order acquisition request command". Since the master table is created according to the operation of the medical facility, the master table may be able to be appropriately updated as needed.

Returning to FIG. 2, the first communication unit 20 performs communication with a client 3 and has an event reception unit 22, a command reception unit 24, and a data transmission unit 26. The event reception unit 22 receives event identification information (event ID) transmitted from the client 3. The command reception unit 24 receives a data acquisition request command transmitted from the client 3. In the above-described example, when the medical worker causes the endoscope observation apparatus to display an order list, the endoscope observation apparatus transmits an order acquisition request command based on the operation input by the medical worker. The data transmission unit 26 transmits data acquired from the management server 5 to the client 3. Data transmission by the data transmission unit 26 is controlled by the data transmission control unit 34.

The second communication unit 50 communicates with the management server 5 and has a command transmission unit 52 and a data reception unit 54. The command transmission unit 52 transmits a data acquisition request command to the management server 5. The command transmission by the command transmission unit 52 is controlled by the command transmission control unit 32. The data reception unit 54 receives the data transmitted from the management server 5 in response to the data acquisition request command.

Figure 4:
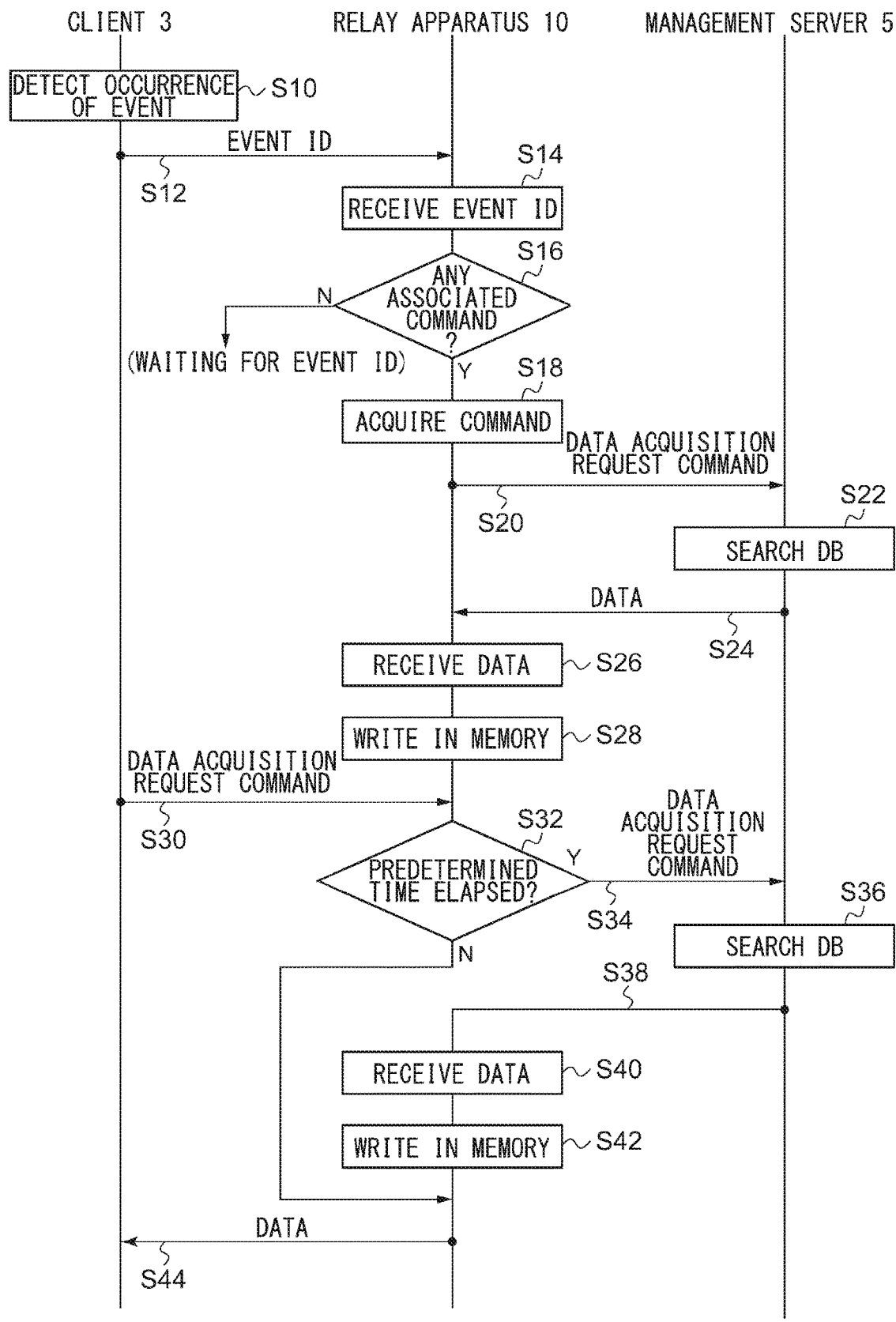
FIG. 4 is a sequence diagram showing the basic operation of the information processing system.

FIG. 4 is a sequence diagram showing the basic operation of the information processing system 1. In this sequence diagram, in order to facilitate the understanding, it is assumed that there is only one client 3 of the same type, and a flow using conditional branching is also included. When the client 3 detects the occurrence of an event (S10), the client 3 transmits the event ID to the relay apparatus 10 (S12).

In the relay apparatus 10, the event reception unit 22 receives the event ID transmitted from the client 3 (S14). The event reception unit 22 provides the event ID that has been received to the command acquisition unit 30. The command acquisition unit 30 refers to the master table recorded in the recorder 38 and determines whether a data acquisition request command is associated with the event ID that has been received (S16). When the client 3 is an endoscope observation apparatus, referring to FIG. 3, a data acquisition request command is not associated with the "scope connected" event, the "examination started" event, the "order list displayed" event, or the "powered off" event. Therefore, when the event IDs of these events are received, the command acquisition unit 30 determines that no data acquisition request command is associated with the event IDs (N in S16) and waits for the next event ID to be transmitted.

On the other hand, when a data acquisition request command is associated with the event IDs that have been received (Y in S16), the command acquisition unit 30 acquires data acquisition request commands associated with the event IDs (S18). Referring to FIG. 3, when acquiring the event ID for "powered on" or "examination ended", the command acquisition unit 30 acquires an order acquisition request command as a data acquisition request command.

The command transmission control unit 32 controls command transmission performed by the command transmission unit 52. When the command acquisition unit 30 acquires a data acquisition request command, the command transmission control unit 32 causes the command transmission unit 52 to transmit the data acquisition request command to the management server 5 (S20).

When the management server 5 receives the data acquisition request command from the relay apparatus 10, the management server 5 searches the DB 6 so as to extract data corresponding to the command (S22). The management server 5 transmits the data extracted in response to the data acquisition request command to the relay apparatus 10 (S24).

In the relay apparatus 10, the data reception unit 54 receives the data transmitted from the management server 5 in response to the data acquisition request command (S26). The cache control unit 36 writes the received data in the memory 40 (S28). At this time, the cache control unit 36 stores, in the memory 40, information on the date and time of the reception of the data by the data reception unit 54 in association with the data. The memory 40 is cache memory that temporarily stores data. As described above, the relay apparatus 10 according to the embodiment has a function of acquiring data in advance, the function being for receiving data that will be required in the future by the client 3 from the management server 5 in advance in response to the occurrence of a predetermined event and for temporarily storing the data in the memory 40.

Thereafter, the client 3 transmits a data acquisition request command to the relay apparatus 10 (S30). The command reception unit 24 receives the data acquisition request command transmitted from the client 3. The data transmission control unit 34 controls data transmission performed by the data transmission unit 26. As the simplest control, when the command reception unit 24 receives a data acquisition request command, the data transmission control unit 34 may cause the data transmission unit 26 to transmit data written in the memory 40 to the client 3 (S44).

FIG. 4 shows a flow for determining whether the data temporarily stored in the memory 40 is new data in order to secure the reliability of the data. The data transmission control unit 34 determines whether or not the command reception unit 24 has received a data acquisition request command before a predetermined time elapses after the data reception unit 54 receives data from the management server 5 (S32). In the memory 40, data is associated with reception date and time information of the data, and the data transmission control unit 34 determines whether or not a predetermined time has elapsed from the reception date and time of the data and the reception date and time of the command in the command reception unit 24.

Order data will now be explained. In most cases, order data is issued for a patient's examination reserved by the previous day. However, order data may be issued for an emergency examination for the day. In a medical facility, even in the case of an emergency examination, it is preferable to issue order data and link examination results such as endoscopic images to the order data. Therefore, even when old order data, for example, data acquired immediately after the start of the examination task is stored in the memory 40, there is a possibility that the order data for an emergency examination is issued and added thereafter.

Therefore, if the command reception unit 24 receives a data acquisition request command from the client 3 before a predetermined time elapses after the data reception unit 54 receives data from the management server 5 (N in S32), the data transmission control unit 34 determines that the data written in the memory 40 is new and reliable and causes the data transmission unit 26 to transmit the data written in the memory 40 to the client 3 (S44). The predetermined time for determining whether the data is new or old is determined depending on the type of the data. For example, in the case of order data, the predetermined time may be set to a period of time of about "five minutes".

On the other hand, if the command reception unit 24 receives a data acquisition request command from the client 3 after the predetermined time has elapsed after the data reception unit 54 has received data from the management server 5 (Y in S32), the data transmission control unit 34 determines that the data written in the memory 40 is old and not reliable and does not cause the data transmission unit 26 to transmit the data written in the memory 40 to the client 3. At this time, the data transmission control unit 34 provides the command acquisition unit 30 with the data request command received by the command reception unit 24. When the command acquisition unit 30 acquires the data acquisition request command, the command transmission control unit 32 causes the command transmission unit 52 to transmit the data acquisition request command to the management server 5 (S34).

When the management server 5 receives the data acquisition request command from the relay apparatus 10, the management server 5 searches the DB 6 so as to extract data corresponding to the command (S36). The management server 5 transmits the data extracted in response to the data acquisition request command to the relay apparatus 10 (S38).

In the relay apparatus 10, the data reception unit 54 receives the data transmitted from the management server 5 in response to the data acquisition request command (S40). The cache control unit 36 overwrites the memory 40 with the received data (S42). The cache control unit 36 stores, in the memory 40, information on the date and time of the reception of the data by the data reception unit 54 in association with the data. When the cache control unit 36 writes the data in the memory 40, the data transmission control unit 34 causes the data transmission unit 26 to transmit the data written in the memory 40 to the client 3 (S44).

As described above, according to the sequence illustrated in FIG. 4, the relay apparatus 10 has already acquired the data from the management server 5 at the time when the client 3 transmits the data acquisition request command through the function of acquiring data in advance of the relay apparatus 10. Therefore, the relay apparatus 10 can transmit the data to the client 3 promptly without having any effect on the communication environment between the relay apparatus 10 and the management server 5.

Although only one client 3 is targeted in the sequence shown in FIG. 4, some medical facilities have a plurality of clients 3 of the same type. For example, some large-scale medical facilities have ten or more endoscopic observation apparatuses.

FIG. 5 shows an example of a timing chart for event notification and command transmission. In this timing chart, the horizontal axis represents a time axis. The clients $3a$, $3b$, $3c$ and $3d$ are devices of the same type and are endoscopic observation apparatuses in this case. The meaning of each arrow in the timing chart is as follows.

Solid Arrow Represented by Combination of E and Number

The notification of an event ID associated with an order acquisition request command is indicated. E1 to E4 indicate the notification of a powered-on event, and E5 indicates the notification of an examination-ended event. In FIG. 5, notification of an event ID not associated with the order acquisition request command is omitted.

Dotted Arrow Represented by Combination of C and Number

The transmission of an order acquisition request command is indicated.

Thick Solid Arrow Represented by Combination of D and Number

The transmission of order data is indicated.

First, a client $3b$ transmits a powered-on notification E1 to the relay apparatus 10. At the time when the relay apparatus 10 receives the powered-on notification E1, the relay apparatus 10 has not stored the order data in the memory 40 yet. Therefore, in the relay apparatus 10, the command transmission unit 52 transmits an order acquisition request command C1 to the management server 5, and the management server 5 transmits order data D1 to the relay apparatus 10. In the relay apparatus 10, when the data reception unit 54 receives the order data D1, the cache control unit 36 writes the order data in the memory 40 in association with a reception time t1.

Before a predetermined time (for example, five minutes) elapses after the time t1, the relay apparatus 10 receives a powered-on notification E2 and an order acquisition request command C2 from a client $3d$, receives an order acquisition request command C3 from a client $3b$, receives a powered-on notification E3 from a client $3c$, and receives a powered-on notification E4 from a client $3a$. In the relay apparatus 10, the command transmission control unit 32 stops command transmission performed by the command transmission unit 52 until the predetermined time elapses from the time t1 at which the data reception unit 54 receives order data from the management server 5.

The command transmission control unit 32 can also transmit an order acquisition request command from the command transmission unit 52 to the management server 5 every time a powered-on notification is received. Thereby, a condition can be created where the latest order data is stored in the memory 40 at the time when a data acquisition request command is transmitted from a client 3. However, when order data is transmitted from the management server 5 every time a powered-on notification is received, the communication load between the relay apparatus 10 and the management server 5 is undesirably increased. Thus, until the predetermined time elapses after time t1, the command transmission control unit 32 stops command transmission performed by the command transmission unit 52 so as to reduce the communication load between the relay apparatus 10 and the management server 5.

When the command reception unit 24 receives a data acquisition request command from a client 3 before the predetermined time elapses after the time t1, the data transmission control unit 34 causes the data transmission unit 26 to transmit data written in the memory 40 to the data transmission unit 26. In this timing chart, the command reception unit 24 has received the order acquisition request command C2 from the client $3d$ and the order acquisition request command C3 from the client $3b$ before the predetermined time has elapsed from the time t1, and the data transmission control unit 34 has caused the data transmission unit 26 to transmit order data D2 to the client $3d$ and order data D3 to the client $3b$. Note that the order data D1, the order data D2, and the order data D3 are the same data.

As described with regard to S32 of FIG. 4, the relay apparatus 10 requests the management server 5 to transmit the latest order data when the predetermined time has elapsed from the time t1 in order to enhance the reliability of the order data written in the memory 40. In the timing chart, time t2 when the command reception unit 24 receives the order acquisition request command C4 from the client $3c$ is the time after the predetermined time has elapsed from the time t1. Thus, the command transmission control unit 32 causes the command transmission unit 52 to transmit an order acquisition request command C5 to the management server 5.

The management server 5 transmits the latest order data D4 to the relay apparatus 10 in response to the order acquisition request command C5. In the relay apparatus 10, when the data reception unit 54 receives order data D4, the cache control unit 36 overwrites the memory 40 with the order data in association with a reception time t3. At the same time, the data transmission control unit 34 causes the data transmission unit 26 to transmit order data D5 to the client 3c. Note that the order data D4 and the order data D5 are the same data.

In this timing chart, the command reception unit 24 has received an order acquisition request command C6 from the client 3a before the predetermined time has elapsed after the time t3, and the data transmission control unit 34 has transmitted order data D6 to the client 3a. Until the predetermined time elapses after the time t3, the command transmission control unit 32 stops command transmission performed by the command transmission unit 52.

Subsequently, at time t4, the event reception unit 22 receives an examination-ended notification E5 from the client 3d. The time t4 represents the time after the predetermined time has elapsed from the time t3. Therefore, the command transmission control unit 32 causes the command transmission unit 52 to transmit an order acquisition request command C7 to the management server 5. The management server 5 transmits the latest order data D7 to the relay apparatus 10 in response to the order acquisition request command C7. In the relay apparatus 10, when the data reception unit 54 receives the order data D7, the cache control unit 36 overwrites the memory 40 with the order data in association with reception time t5.

As described above, when the event reception unit 22 receives the examination-ended notification E5 and the command reception unit 24 receives the order acquisition request command C4 after a predetermined time has elapsed after the data reception unit 54 receives order data from the management server 5, the command transmission control unit 32 causes the command transmission unit 52 to transmit a data acquisition request command. As described, the relay apparatus 10 performs a process of acquiring data so as to store the latest data in the memory 40 while avoiding an excessive communication load with the management server 5.

As shown in FIG. 5, the command transmission control unit 32 controls the transmission of a data acquisition request command that is based on an event notification (actually the notification of an event ID) from a client 3 and the transmission of a data acquisition request command that is based on a data acquisition request command from a client 3. More specifically, the order acquisition request commands C1 and C7 are based on an event notification from a client 3, and the order acquisition request command C5 is based on a data acquisition request command from a client 3.

The transmission of a data acquisition request command based on an event notification is for the purpose of acquiring data in advance in this case. Thus, it is not necessary to perform the transmission even under an environment that is not suitable for command transmission. For example, there is little need to acquire data in advance even in the case where the communication environment between the relay apparatus 10 and the management server 5 is significantly deteriorated. Therefore, the command transmission control unit 32 may measure the communication speed between the relay apparatus 10 and the management server 5 and determine, based on the result of comparing the measured communication speed and a predetermined reference speed, the propriety of transmitting a data acquisition request command based on an event notification.

On the other hand, the transmission of a data acquisition request command based on a data acquisition request command from a client 3 needs to be performed immediately regardless of the quality of the communication environment. Thus, in the case where the command transmission control unit 32 causes the command transmission unit 52 to transmit a data acquisition request command to the management server 5 when the command reception unit 24 receives the data acquisition request command from the client 3, the command transmission control unit 32 may cause the data acquisition request command to be transmitted to the management server 5 regardless of the result of comparing the measured communication speed and the predetermined reference speed.

Described above is an explanation on the present invention based on the embodiments. These embodiments are intended to be illustrative only, and it will be obvious to those skilled in the art that various modifications to constituting elements and processes could be developed and that such modifications are also within the scope of the present invention.

In the embodiments, it has been described that when it is determined that a predetermined time has elapsed from the reception date and time of data, the command transmission unit 52 transmits a data acquisition request command to the management server 5, the data reception unit 54 receives the data from the management server 5, and the cache control unit 36 overwrites the memory 40 with the data that has been received. In an exemplary variation, the cache control unit 36 may automatically delete data from the memory 40 when a predetermined time has elapsed from the reception date and time of the data. In this exemplary variation, when the command reception unit 24 receives a data acquisition request command from a client 3, the data transmission control unit 34 may check whether or not data is stored in the memory 40 and cause the data to be transmitted from the data transmission unit 26 if the data is stored, and the command transmission control unit 32 may cause a data acquisition request command to be transmitted from the command transmission unit 52 if the data is not stored.

In the embodiments it has been described that a client 3 is a device in a medical facility that performs an endoscopic examination. Alternatively, the client 3 may be a device in a medical facility that performs a different examination or surgery. The client 3 is not limited to a device in a medical facility and may be a device used in facilities of various fields.

What is claimed is:

1. A relay apparatus for relaying communication between a client and a server, comprising:
   a processor comprising hardware; and
   a recorder that records event identification information and a data acquisition request command in association with each other,
   wherein the processor is configured to:
      receive event identification information transmitted from a client;
      acquire, from the recorder, a data acquisition request command associated with the event identification information that has been received;
      transmit the data acquisition request command to a server upon acquiring the data acquisition request command associated with the event identification information that has been received;
receive data transmitted from the server in response to the data acquisition request command;
write the data that has been received in a memory;
receive a data acquisition request command transmitted from the client; and
transmit the data written in the memory to the client, and
wherein the processor is further configured to transmit, upon receiving the data acquisition request command from the client before a predetermined time elapses after the reception of data from the server, the data written in the memory to the client.

2. The relay apparatus according to claim 1,
wherein the relay apparatus relays communication between a plurality of clients and the server.

3. The relay apparatus according to claim 1,
wherein the processor is configured to:
not transmit the data acquisition request command to the server before the predetermined time elapses after the reception of the data from the server.

4. The relay apparatus according to claim 3,
wherein the processor is configured to:
transmit, upon receiving the event identification information from the client or the data acquisition request command from the client after the predetermined time has elapsed after the reception of the data from the server, the data acquisition request command to the server.

5. The relay apparatus according to claim 4,
wherein the processor is configured to:
overwrite, upon receiving the data from the server, the memory with the data that has been received.

6. The relay apparatus according to claim 1,
wherein the processor is configured to:
measure the communication speed between the relay apparatus and the server and determine, based on the result of comparing the measured communication speed and a predetermined reference speed, the propriety of transmitting the data acquisition request command based on the event identification information.

7. The relay apparatus according to claim 6,
wherein the processor is configured to:
transmit, in the case of transmitting the data acquisition request command to the server when receiving the data acquisition request command from the client, the data acquisition request command to the server regardless of the result of comparing the measured communication speed and the predetermined reference speed.

8. The relay apparatus according to claim 1,
wherein the relay apparatus relays communication between a plurality of clients that are devices connected to a local area network of a medical facility and an external server installed outside the local area network.

9. A relay apparatus for relaying communication between a client and a server, comprising:
a processor comprising hardware; and
a recorder that records event identification information and a data acquisition request command in association with each other,
wherein the processor is configured to:
receive event identification information transmitted from a client;
acquire, from the recorder, a data acquisition request command associated with the event identification information that has been received;
transmit the data acquisition request command to a server upon acquiring the data acquisition request command associated with the event identification information that has been received;
receive data transmitted from the server in response to the data acquisition request command;
write the data that has been received in a memory;
receive a data acquisition request command transmitted from the client; and
transmit the data written in the memory to the client, and
wherein the processor is further configured to measure the communication speed between the relay apparatus and the server and determine, based on the result of comparing the measured communication speed and a predetermined reference speed, the propriety of transmitting the data acquisition request command based on the event identification information.

10. The relay apparatus according to claim 9,
wherein the processor is configured to:
transmit, in the case of transmitting the data acquisition request command to the server when receiving the data acquisition request command from the client, the data acquisition request command to the server regardless of the result of comparing the measured communication speed and the predetermined reference speed.

* * * * *